US008530695B2

(12) United States Patent
Reunanen et al.

(10) Patent No.: US 8,530,695 B2
(45) Date of Patent: Sep. 10, 2013

(54) PROCESS FOR RECOVERY OF FORMIC ACID

(75) Inventors: Jarmo Reunanen, Oulu (FI); Pekka Oinas, Kokkola (FI); Timo Nissinen, Ylojarvi (FI)

(73) Assignee: Kemira Oyj, Helsinki (FI)

( * ) Notice: Subject to any disclaimer, the term of this patent is extended or adjusted under 35 U.S.C. 154(b) by 357 days.

(21) Appl. No.: 12/989,001

(22) PCT Filed: Apr. 21, 2009

(86) PCT No.: PCT/FI2009/050311
§ 371 (c)(1),
(2), (4) Date: Dec. 17, 2010

(87) PCT Pub. No.: WO2009/130386
PCT Pub. Date: Oct. 29, 2009

(65) Prior Publication Data
US 2011/0137051 A1 Jun. 9, 2011

(30) Foreign Application Priority Data
Apr. 21, 2008 (FI) ................................... 20085336

(51) Int. Cl.
*C07C 51/00* (2006.01)
*C07D 307/50* (2006.01)

(52) U.S. Cl.
USPC ............ 562/515; 549/489; 562/577; 562/609

(58) Field of Classification Search
USPC .......................... 562/515, 577, 609; 549/489
See application file for complete search history.

(56) References Cited

U.S. PATENT DOCUMENTS

| | | | |
|---|---|---|---|
| 2,257,389 | A | 9/1941 | Maccallum |
| 2,684,982 | A | 7/1954 | Dunlop |
| 2,813,900 | A | 11/1957 | Dunlop et al. |
| 4,217,460 | A | 8/1980 | Hohenschutz et al. |
| 4,401,514 | A | 8/1983 | Kanzler et al. |
| 4,692,219 | A | 9/1987 | Berg |
| 5,399,751 | A | 3/1995 | Gentry et al. |
| 6,054,611 | A | 4/2000 | Farone et al. |
| 2003/0013926 | A1 | 1/2003 | Saruwatari |
| 2003/0036664 | A1 | 2/2003 | Auer et al. |
| 2003/0233011 | A1 | 12/2003 | Fagan et al. |
| 2005/0172858 | A1 | 8/2005 | Schonherr et al. |
| 2007/0100162 | A1 | 5/2007 | Petrus et al. |
| 2012/0296118 | A1 | 11/2012 | Heinz et al. |

FOREIGN PATENT DOCUMENTS

| | | |
|---|---|---|
| CN | 1254705 A | 5/2000 |
| CN | 101160279 A | 4/2008 |
| DE | 1518686 | 4/1969 |
| EP | 0038317 A1 | 4/1980 |
| EP | 0365665 B1 | 7/1995 |
| EP | 0873294 B1 | 5/1996 |
| FI | 117633 | 12/2006 |
| WO | 0146520 A1 | 12/2000 |
| WO | 02053521 A1 | 7/2002 |
| WO | 02053524 A2 | 7/2002 |
| WO | 02053829 A1 | 7/2002 |
| WO | 2004006689 A1 | 1/2004 |
| WO | 2005070867 A1 | 8/2005 |
| WO | 2009130386 A1 | 10/2009 |
| WO | 2009130387 A2 | 10/2009 |

OTHER PUBLICATIONS

English Abstract for EP0038317A1, 1 pg., (1980).
English Abstract for CN1254705A, Supplied by espacenet database, http://v3.espacenet.com/publicationDetails/biblio?DB=EPODOC &adjacent=true&locale . . . ; 1 pg., (2000).
English Abstract for WO0146520, 1 pg., (2000).
English Abstract for WO 02/053524A2, 1 pg., (2000).
Abstract for FI117633, 2 pgs., (2006).
Hayes, Daniel J., et al. "The Biofine Process—Production of Levulinic Acid, Furfural, and Formic Acid for Lignocellulosic Feedstocks", Biorefineries—Industrial Process and Products, Status Quo and Future Directions, vol. 1, 2006 Wiley-VCH Verlag GmbH & Co., pp. 139-164.
International Preliminary Report on Patentability for Application No. PCT/FI2009/050311, Priority Date: Apr. 21, 2008, date of mailing Apr. 21, 2008, 8 pgs.
Reply to Written Opinion for Application PCT/FI2009/050311, Due date: Feb. 21, 2010, 3 pgs.
Search Report for Finland Application No. 20085336, dated Oct. 9, 2008, 1 pg.
Written Opinion of International Searching Authority for Application No. PCT/FI20091050311; International Filing Date: Apr. 21, 2009; Mail date: Jul. 7, 2010, 8 pgs.
Office Action in Corresponding CN Patent Application No. 200980114171.4, (2012).
English Abstract for WO02053521, 1 pg., (2002).
English Abstract for WO2006108652, 1 pg., (2006).
International Preliminary Report on Patentability for Application PCT/FI2009/050312; Filing Date: Apr. 21, 2009, 15 pgs.
Reply to Written Opinion dated May 12, 2010 for Application PCT/FI2009/050312 in regarding to Written Opinion issued Feb. 12, 2010; 4 pgs.
Written Opinion for Application No. PCT/FI2009/050312; Filing Date: Apr. 21, 2009, 16 pgs.

*Primary Examiner* — Bernard Dentz
(74) *Attorney, Agent, or Firm* — Thomas Horstemeyer, LLP

(57) ABSTRACT

The invention relates to a process for the recovery of concentrated high purity formic acid having a concentration of at least 50%, most preferably at least 95%, from biomass wherein an aqueous liquid mixture containing levulinic acid and possibly furfural is subjected to a liquid-liquid extraction step, followed by the recovery of furfural, formic acid and levulinic acid.

14 Claims, 4 Drawing Sheets

PROCESS FOR RECOVERY OF FORMIC ACID

BACKGROUND

The present invention relates to the recovery of concentrated formic acid from biomass.

Biomass such as pulp, waste paper, paper mill sludge, urban waste paper, agricultural residues, rice straw, woody plant, cotton materials and cellulose fines from papermaking etc. may be reconverted into useful platform chemicals. This requires sufficient economics and reasonable process feasibility for the processes to be used for the recovery of industrially interesting chemicals.

A variety of interesting bulk chemicals is accessible by the acid-catalyzed hydrolysis of biomass such as cellulose which is a natural polymer consisting of glucose units and abundantly available on earth. One attractive option is the conversion of glucose to levulinic acid (IUPAC systematic name: 2-hydroxypropanoic acid i.e. 4-oxopentanoic acid i.e. acetyl propanoic acid) by acid treatment. In the following text, the trivial name levulinic acid is used as the name of this compound. Levulinic acid is a versatile building block for fuel additives, polymer and resin precursors.

Two different approaches are commonly applied for the acid-catalyzed hydrolysis of cellulose. The first one uses high concentrations of mineral acids (e.g., 15 to 16 N HCl or 31 to 70% by weight $H_2SO_4$) as catalysts at low operating temperatures (20 to 50° C.). The major drawbacks are the high operating cost of acid recovery and the use of expensive construction material for both the hydrolyser and the acid recovery system. The second approach uses highly diluted acids at high operating temperatures (170 to 240° C.). This method is favoured and research studies applying this approach are abundant.

There are several publications on conversion of biomass to carboxylic acids but none of them simultaneously recover both levulinic acid and formic acid economically and selectively with sufficient purity. Most of the publications disclose methods for converting carbohydrate material to organic acids such as levulinic acid and formic acid, and furfural. A purification process especially to formic acid is not described in the procedures of converting biomass in the literature.

Several publications disclose the separation and recycling of formic acid or more typically carboxylic acids in general, and levulinic acid or furfural from the mixtures thereof. The actual recovery of formic acid, and especially recovery of concentrated formic acid originating from biomass with suitable purity for further applications could not be found.

An example of a highly diluted acid process is disclosed in EP 365 665, EP 873 294 and by Hayes et al. in Kamm, Gruber, Kamm: Biorefineries—Industrial Processes and Products, Vol. 1, p. 139-164 and references therein. This is a commercialized technology that uses two-step hydrolysis with dilute mineral acid such as sulphuric acid to break down biomass containing carbohydrates to give intermediate chemicals such as hydroxymethylfurfural or furfural that can be further converted to levulinic acid and other chemical products such as tetrahydrofuran. Benefit of this biomass conversion process is to reduce the tons of trash in the nation's landfills, as well as reduce the dependence on imported oil used to produce petrochemicals. While levulinic acid can be synthesized by several methods, frequently they form large amounts of by-products and intractable materials, or require expensive feedstocks. However, because of its two-reactor system, this process eliminates many of the existing problems with levulinic acid production including by-product formation and the resulting separation problems.

EP 873 294 discloses a process wherein:

The carbohydrate containing material such as cellulose, hemicellulose and starch is mixed with an acid-water solution to form slurry.

Cellulose and starch containing carbohydrates such as glucose, galactose, or similar molecules are split into hexose monomers in acidic conditions. As the reaction continues at elevated temperature and pressure, the hexose monomers are converted to hydroxymethyl furfural and other intermediates and further into levulinic acid and formic acid. The reaction is carried out in a two-stage chemical reactor. The first stage is a short-contact tubular reactor operating at 210 to 230° C. and at a pressure of approximately 30 bar and a second stage reactor is a continuous stirred tank reactor with longer residence time operated at 195 to 215° C. and at a pressure of approximately 15 bar. If hemicellulose containing material is involved as feedstock, it is converted both to hexose and pentose monomers and oligomers. The pentoses degrade further to furfural.

The components with highest volatility, water, formic acid and furfural are vaporized and condensated from the mixture by adjusting the temperature and pressure.

The less volatile levulinic acid containing fraction is separated from lignin containing solid material by filtration.

In the article of Hayes et al. it is mentioned that the processing of cellulose yields approximately 50% of levulinic acid, 20% of formic acid, and 30% of tars calculated from the mass of 6-carbon sugars. The mass yield of furfural from 5-carbon sugars is approximately 50%. Thus, each ton of levulinic acid produced produces 400 kg of formic acid. There is clearly a need to recover efficiently and simultaneously formic acid parallel to the other platform chemicals.

US 2007/0100162 concerns the production of levulinic acid and discloses that the liquefication of lignocellulosic or cellulosic material can be facilitated by incorporating a solvent comprising furfural, levulinic acid, a compound obtainable from furfural or a compound obtainable from levulinic acid by various types of reactions, such as hydrogenation. The solid content can then be up to 50% in the feedstock while in EP 873 294 the slurry concentration of 20 to 40% was required. There is no teaching on how to recover concentrated formic acid from aqueous solution produced in this process.

U.S. Pat. No. 4,401,514 discloses a method for the recovery or extraction of chemicals such as furfural, formic acid, acetic acid and other organic chemicals from acidic hydrolysates of plant or vegetable matter. The object of this disclosure is to provide an extremely energy saving manner of extracting recovered furfural. During the furfural recovery steps of the method, a mixture containing furfural, formic acid, acetic acid and water is obtained. This mixture may further be distilled to separate an azeotrope of water and formic acid including some residual acetic acid and furfural and a mixture comprising furfural and acetic acid. In order to separate formic acid as a concentrated acid from its azeotrope, considerable additional amount of energy is required. Furthermore, there is no teaching on the influence or handling of levulinic acid if this should be present in such mixtures.

WO2005070867 discloses a reactive extraction method for the recovery of levulinic acid from an aqueous mixture containing e.g. levulinic acid, formic acid and furfural wherein the mixture is first contacted with a liquid esterifying water-immiscible alcohol in the presence of a catalyst at 50 to 250° C. to form esters of levulinic acid and formic acid. These esters remain in organic phase together with the alcohol and furfural. According to the invention, the desired levulinate and all the other compounds can be separated by applying different sequential separation methods, distillations such as e.g. reactive distillation from the organic phase. Formic acid ester is converted to formic acid by acid hydrolysis and separated simultaneously by distillation from the alcohol. This separation process has not been experimentally verified and is known to be very complex. Formic acid is equally obtainable as an ester from the organic phase requiring further processing for the recovery of the pure acid.

US 20030233011 discloses a method for treating a mixture obtained from biomass hydrolysis as follows: The solid phase is removed first and furfural is removed by decantation. Thereafter, the mixture comprising levulinic acid, formic acid and water is contacted with an olefin to form esters of levulinic acid and formic acid. These esters are then extracted with a water-immiscible organic solvent. After separating the aqueous layer, the esters are separated from the solvent by distillation and the extraction solvent is recycled. The solvent may be chosen so that it can be used as a fuel additive parallel to esters of levulinic and formic acid. The reaction with olefins can be made simultaneously with the extraction process according to the reference. This method does not involve recovery of formic acid in acid form.

U.S. Pat. No. 6,054,611 discloses a process operated at conditions with considerably lower temperatures than in EP 873 294, resulting in much longer reaction time and lower capacity. The separation of levulinic acid, furfural and water is performed by chromatographic methods. Conventional distillations are also mentioned in example 1, but the stream doesn't include formic acid. Levulinic acid is obtained as alkyl levulinate.

FI 117633 discloses a method for recovering and recycling a mixture of formic acid, acetic acid, water and furfural in the pulping process. This mixture does not include levulinic acid. The separation is carried out by a series of distillation columns using furfural as a distillation aid to separate the main part of water as furfural-water azeotrope. In the distillation, the said mixture incorporates several azeotropes making the distillation to pure products complicated. The mixture of formic acid and acetic acid is recycled to pulping process and it is neither disclosed nor considered relevant how to separate these acids as pure products.

In many cases, the carboxylic acids generated as the result of biomass degradation are obtained as dilute aqueous solutions. Distillation is an obvious method to purify isolated substances from aqueous solutions, but distillation as such is not the best option as far as energy-efficiency is considered. Besides, some of the components such as formic acid may form azeotropes with water making the separation into pure components difficult. The separation can be accomplished by arranging several distillation processes and equipment parallel or in series but then the energy cost of separation and equipment will become high. Furthermore, separation into single components is not feasible without using large columns with a high number of distillation stages or trays.

Separation of various chemicals may be based on liquid-liquid extraction processes. Even carboxylic acids have been separated from dilute aqueous solutions with extraction solvents insoluble or slightly soluble in water, or with solvent mixtures. However, the efficiency of extraction agents is typically not satisfactory enough to yield pure components.

U.S. Pat. No. 5,399,751 by contrast discloses a method for the recovery of formic acid from an aqueous solution containing acetic acid, formic acid and water. There is neither furfural nor levulinic acid present in this mixture. The procedure is described as follows: 1) The aqueous solution is contacted with a solvent consisting of mixed trialkyl phosphine oxides in a liquid-liquid extraction column producing two phases where the aqueous raffinate is low in acids and solvent. The aliphatic acids are extracted in the organic solvent phase. This solvent has a low miscibility and solubility in water. Cyanex 923 manufactured by Cytec Industries containing said mixture is used in the examples as the liquid extracting agent. 2) The solvent rich in acids is dehydrated to remove most of water in the first distillation column. 3) The bottoms of the first column is directed to second column in which the acids are stripped out from the solvent that is recycled back to the extraction stage. 4) The mixture of formic acid and acetic acid is splitted to separate fraction in the third distillation column. No advice is provided by this disclosure on the influence and possible treatment of mixtures containing chemicals such as furfural or levulinic acid, derived from biomass.

EP 0 038 317 discloses a method for the extraction of furfural, formic acid, and acetic acid from acid hydrolysates retrieved from biomasses, particularly from spent sulphate lyes. The distillate similar to the one disclosed in EP 873 294 from the hydrolysis reactor containing furfural, acetic acid, formic acid and water is subjected to liquid-liquid extraction. A mixture of trioctyl phosphine oxides in aliphatic hydrocarbon is applied as extracting agent for the extraction of mentioned organic compounds. Water is removed as the raffinate phase and the organic extractant phase is subjected to a series of evaporation and distillation processes to recover furfural and acetic acid as separate streams. The remaining impure mixture containing formic acid fraction is recycled back to biomass hydrolysis. Formic acid or concentrated formic acid is not obtained as a pure product.

The abstract of CN1254705 retrieved from WPINDEX AN 2000-506302 [46] discloses a method for separating and concentrating formic acid with phosphorus-contained extraction reagent in kerosene to prepare a solvent mixture. By distillation of solvent phase, the mass concentration of formic acid is more than 85% by this invention. The bottom solvent from distillation can be reused. The content of the original mixture and the effects of other components in distillation and extraction is not unveiled.

WO0146520 treats waste liquors containing carboxylic acids (mainly formic acid) and water and lignins and traces of furfural and acetic acid, from pulp production such as Milox and Acetosolv processes with extraction by ethers such as di-isopropyl ether. After the extraction the extracting reagent is distilled out from solution giving formic acid as the residual product. Formic acid and acetic acid are not separated. Further, furfural is mentioned but its behaviour and influence on distillation and extraction is not disclosed.

Several other publications are available on the separation of carboxylic acids and acid mixtures such as acetic acid and formic acid from aqueous mixtures thereof. None of these methods describe an economically feasible way to recover formic acid as concentrated acid from biomass or recovery together with levulinic acid and/or furfural from mixtures thereof.

In WO02053524 organic acids such as formic acid and acetic acid are extracted by ethers such as di-isopropyl ether (like in WO0146520). The extracting agent is recovered by distillation. The organic acids are recovered as the residue of distillation. In the separation of acetic acid from formic acid a distillation aid such as cyclopentane is used to break the azeotrope. Furfural is however not included.

The solution obtained from biomass degradation, such as hydrolysis at elevated temperature and pressure can contain furfural if the raw material includes pentoses. Furfural in these cases can be converted to its derivatives, such as furfuryl alcohol, methyl furfuryl alcohol, methylfuran, furoic acid, furfurylamine, furan, and their further derivatives. Catalytic hydrogenation of furfural to methyl furan and further into methyltetrahydrofuran or to furfuryl alcohol and further into levulinic acid is mentioned in the literature.

Prior art discloses several ways of recovering industrially valuable components from biomass degradation including furfural or levulinic acid. Aqueous carboxylic acids or mixtures thereof may be separated and/or circulated back to earlier processes stages. However, an economical and energy efficient method for technically feasibly recovering concentrated formic acid from a mixture containing other aliphatic acids such as levulinic acid and/or furfural that emerge in the reactive pre-treatment of biomass has not been available.

The dilute aqueous phase together with a mixture containing levulinic acid or levulinic acid and furfural together with formic acid has rendered it very difficult to recover concentrated formic acid economically from a mixture thereof.

The objective of the present invention is to economically and efficiently recover concentrated formic acid from a biomass degradation mixture.

A further objective of the present invention is to economically and efficiently recover concentrated formic acid together with levulinic acid and optionally furfural from an aqueous mixture thereof.

SUMMARY OF THE INVENTION

The present invention provides an industrially suitable method for the economical and efficient recovery of formic acid in a form as concentrated as possible from a mixture that contains other aliphatic acids such as levulinic acid or furfural originating from the reactive treatment of biomass. Since both formic acid and furfural form azeotropes with water, the separation of formic acid as a concentrated platform chemical by distillation has been considered neither easy nor energy-efficient.

The present inventors found that a pre-treatment process by first removing the excess water from the dilute liquid mixture originating from the biomass degradation containing formic acid, levulinic acid and furfural by liquid-liquid extraction and subsequently recirculating the remaining residual water suitably facilitates the distillation of formic acid to give a concentrated industrial grade platform chemical. Especially, it was found out that prior to formic acid recovery distillation, in the distillation of furfural azeotrope a certain amount of water is essential to form the furfural-water azeotrope and recycling of water to feed stream after phase separation of the condensate could be utilized to adjust the amount of water required. The separation of essential portion of water from the organic stream directed further to formic acid recovery distillation was found useful since concentrated formic acid was desired as the outcome in this invention.

The present invention provides a method for efficient separation and recovery of concentrated formic acid from an aqueous liquid mixture containing levulinic acid and optionally furfural obtained by biomass degradation as defined by claim 1.

The benefits of the method described are that formic acid is obtained as an essentially pure product in a concentrated form having a concentration of at least 50% by weight, preferably at least 80% by weight, more preferably at least 85% by weight, most preferably at least 90% such as 95% by weight. The obtained concentration is dependent on the amount of water in the mixture wherefrom formic acid is to be separated and the chosen operating parameters such as temperature, pressure, the energy input for the separation process, feed rate and reflux ratio in e.g., distillation. The term reflux ratio refers to the ratio of the amount of condensated mixture that goes back to the top of the distillation column to the amount of condensate that is withdrawn out to the receiving vessel. The higher the reflux ratio, the more vapor/liquid contact can occur in the distillation column. Thus higher reflux ratios mean higher purity of the distillate and consequently slower collection rate for the distillate.

Levulinic acid is recovered as a concentrated acid, preferable in concentrations at least 50% by weight, preferably at least 80% by weight, more preferably at least 85% by weight, most preferably at least 90% by weight, especially such as at least 95% by weight, or as salt thereof, i.e. levulinate. A part of the levulinic acid is preferably recycled back to the hydrolysis process or to further purification processes.

Furthermore, if the biomass to be degraded contains pentoses, furfural is recovered, typically parallel to levulinic acid. The recovery is carried out by an azeotropic distillation, such as for example distilling a mixture containing about 68% by weight water and about 32% by weight furfural at a pressure of 1 atm and subsequent phase separation to give concentrated furfural, preferably in a form having a concentration of at least 85% by weight, more preferably at least 90% by weight, most preferably at least 95% by weight, the balance being essentially water.

Thus obtained concentrated formic acid is readily usable for its conventional applications such as chemical reactant for example in textile dyeing and finishing, anti-bacterial and disinfection chemical, lime scale remover, leather tanning chemical, silage additive or preservative component. The product may be further purified by conventional means for applications requiring specific purity such as pharmaceuticals. Furthermore, it may be used in production of formic acid derivatives, such as formate salts or esters for various applications.

The obtained furfural is commonly used as a solvent in petrochemical refining to extract dienes. Furfural may be used as such or as a derivative like for example furfuryl alcohol, or together with phenol, acetone, or urea to make solid resins. Furfural is also used as a chemical intermediate in the production of furan and tetrahydrofuran.

DETAILED DESCRIPTION OF THE INVENTION

Figure 1:
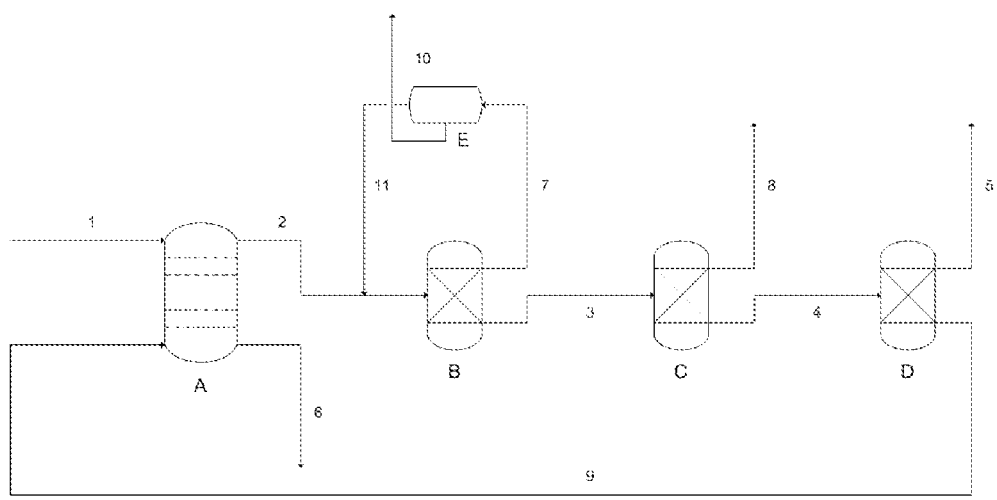
FIG. 1 is a schematic figure of a process for production of concentrated formic acid, furfural and levulinic acid wherein extracting agent is used, the boiling point of which is higher than that of levulinic acid.

By the term "biomass" in this invention, it is meant pulp, waste paper, paper mill sludge, urban waste paper, agricultural residues, rice straw, woody plant, cotton materials and cellulose fines from papermaking or any biomaterial which may be converted into formic acid and levulinic acid and optionally furfural. Preferably, carbohydrate containing cellulosic materials such as waste wood, waste paper, primary sludges from paper manufacturing, are used as biomass raw materials. Optionally, the carbohydrate containing cellulosic biomass material contains components that in biomaterial hydrolysis are at least partly converted into furfural, such as pentoses.

This biomass may be degraded or treated by any known method to provide a mixture containing suitable precursors for formic acid and levulinic acid and optionally furfural. Preferably, the mixture to be treated by the method according to the invention is obtained by acidic hydrolysis since this process has proved to be a practical solution and technologically feasible compared to, for example, biological or bacterial treatments. The mixture to be treated can be obtained by inorganic acid-hydrolysis treatment at elevated operating temperatures and corresponding pressures, preferably at a temperature from 150 to 250° C. and at a pressure from 10 to 40 bar.

By the term "mixture" in the present invention, it is meant an aqueous liquid mixture. This mixture is suitable for further processing by the method of the invention described below. Preferably, this mixture is suitable for liquid-liquid extraction process by conventional liquid-liquid extraction means allowing the presence of some solids, preferably less than 5%, more preferably less than 1% by weight, but wherein the amount of solids needs to be low enough for not disturbing the extraction process. This mixture preferably includes formic acid up to 10% by weight, preferably, levulinic acid up to 15% by weight and optionally furfural up to 10% by weight. The mixture may further include inorganic acid(s) and/or acetic acid. Acetic acid may be formed in the degradation of hemicellulose through pentosan sugar fraction. More preferred concentrations are for formic acid from 1 to 5% by weight, for levulinic acid from 3 to 8% by weight, and optionally for furfural from 1 to 5% by weight and optionally for inorganic acids up to 10%, preferably from 1 to 5% by weight, the balance being water.

The method provided by the present invention comprises separating and recovering at least concentrated formic acid from an aqueous liquid mixture containing levulinic acid and optionally furfural obtained by biomass degradation by using at least the following steps:

The mixture containing formic acid and levulinic acid and optionally furfural is subjected to liquid-liquid extraction by employing an extracting agent whereby an organic phase comprising the extracting agent, formic acid, levulinic acid and optionally furfural and an aqueous phase comprising essentially water, preferably further containing inorganic acid(s), are obtained. The aqueous phase is separated and removed from the organic phase by gravitation.

ii Optionally, furfural is separated and recovered, preferably by distillation and gravitational separation, from the organic phase. This organic phase contains furfural, formic acid and levulinic acid obtained from step i after the removal of the aqueous phase.

Formic acid is recovered by distillation as concentrated acid, in a concentration of at least 50% by weight, from the organic phase. This organic phase contains formic acid and levulinic acid from step i or optionally from step ii.

Levulinic acid or levulinate salt is recovered from the organic phase. This organic phase contains levulinic acid obtained from step iii by distillation.

Preferably, the method according to the invention comprises a further recycling step v of recovering and recycling said extracting agent which is still present in the organic phase after the removal of formic acid, levulinic acid and optionally furfural. The extracting agent is recycled back to the extraction step i as infeed. The extracting agent may be obtained from the distillation in step iv either as the bottom product (for example, FIG. 1, flow 9) or as the condensed overhead product (FIG. 2, flow 9). Alternatively, the extracting agent is obtained from the decantation tank in step iv as the bottom product (see FIG. 3, flow 7) or as the filtrate from filtration (see FIG. 4, flow 7).

Preferably, the step ii comprises a further recycling step vi wherein the residual aqueous component (FIG. 1, flow 11) from the separation of furfural is recirculated back to step ii infeed.

Preferably, the method according to the invention comprises a further recycling step vii wherein the aqueous phase (FIG. 1, flow 6) separated in step i is recycled back to the previous processes for biomass degradation. This aqueous phase may be recycled back to, for example, the biomass acid-hydrolysis. The aqueous phase to be recycled may comprise still some formic acid, levulinic acid and furfural, if present in the mixture of step i. Most preferably, the aqueous phase to be recycled contains essentially no organic acids. The aqueous phase comprises preferably at least one inorganic acid necessary in the acid-hydrolysis.

Extraction is a process that separates components based upon chemical differences rather than differences in physical properties. Extraction involves the contacting of a solution with an extracting agent, another reagent and/or solvent that is immiscible with the original one. The solutes contained in the solution are soluble in the extracting agent. Two phases are formed after the addition of the extracting agent, due to the differences in densities between the phases. The extracting agent is chosen in such a way that the solute in the solution has more affinity towards the added extracting agent. Therefore, mass transfer of the solute from the solution to the extracting agent occurs. Liquid-liquid extraction was found useful in removing most of the water from the dilute acidic solution forming the aqueous liquid mixture of the present invention.

Figure 2:
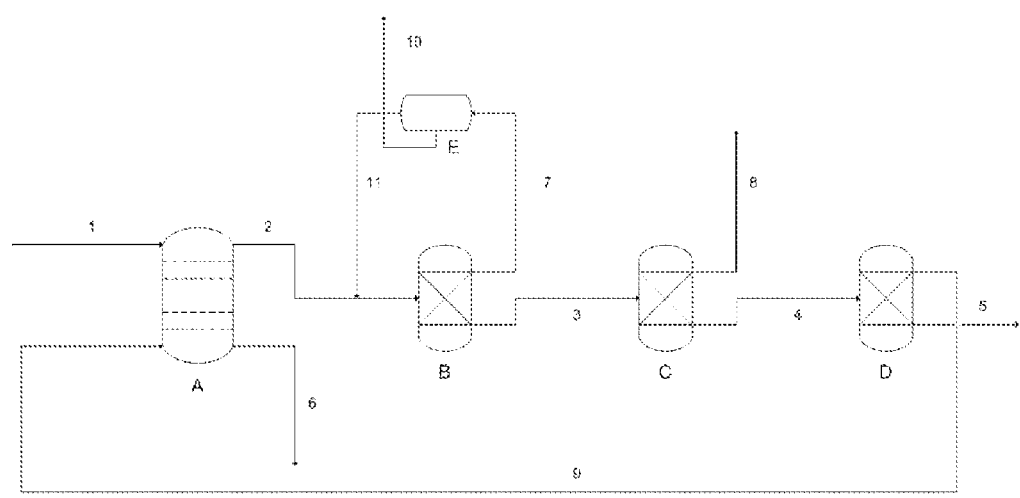
FIG. 2 is a schematic figure of a process for production of concentrated formic acid, furfural and levulinic acid, wherein an extracting agent is used, the boiling point of which is lower than that of levulinic acid.

In the first step, the mixture originating from the biomass degradation (FIG. 1, flow 1) comprising formic acid, levulinic acid, water and optionally furfural is directed to conventional liquid-liquid extraction means (FIG. 1, A). In the selection of appropriate equipment for liquid-liquid extraction, it is preferred that the contacting area of mass transfer is maximized and the flows of the separated phases are properly adjusted for maximum solute recovery. The equipment preferred for liquid-liquid extraction is the following: first, contacting columns can be used for most liquid-liquid extraction systems. In these columns, the internal packings, trays, or sprays increase the surface area for the two liquid phases to intermingle. This also allows for a longer flow path that the solution can travel through in the contacting column. In the selection of the column packing, it is necessary to select such a material that is best wetted by the continuous phase. The flow in a column should be counter-current. Second, centrifugal contractors are preferred for systems for liquid-liquid extractions where the density difference between the phases is small, preferably less than 4%. This type of system should be utilized in processes requiring multiple equilibrium stages. Third, mixer-settlers with one equilibrium stage in each cell usually requiring a large-volume vessel and a high liquid demand may be utilized as well.

Whatever the selection of the equipment is, operating variables such as operating temperature, operating pressure, feed flow rates and compositions and the temperature and pressure of the entering streams in an liquid-liquid extraction process are to be assigned. The pressure and temperature must be selected so that all components remain in the liquid phase. Preferably, the pressure in the liquid-liquid extraction is less than 3 bar, more preferably ambient pressure is used such as 1 bar, and the temperature is preferably less than 100° C., more preferably from 20 to 100° C., most preferably from 30 to 60° C.

The mixture (FIG. 1, flow 1) introduced to step i containing formic acid, levulinic acid, water and preferably comprising further at least one inorganic acid, and optionally furfural is subjected to liquid-liquid-extraction by employing an water-immiscible or slightly water-soluble organic extracting agent into which the organic compounds are transferred by dissolution. As the result, two separate phases with different densities are obtained; namely the organic phase comprising of the extracting agent, formic acid, levulinic acid and optionally furfural, and an aqueous phase comprising essentially of water, preferably comprising further at least one inorganic acid, are obtained.

The ratio of the aqueous liquid mixture to the extracting agent to be fed into the extraction step i should be from 1:1 to 4:1, preferably from 2:1 to 4:1.

The inorganic acid(s) in the mixture may originate from the previous biomass degradation processes such as acid hydrolysis. The amount of inorganic acid in the mixture is preferably up to 10% by weight, more preferably from 1 to 5%. Preferably this inorganic acid is sulphuric acid. The acid is separated in the extraction step i and essentially all of it, preferably at least 95%, remains in the separated aqueous phase. This acid may be recycled back to, for example, the acid hydrolysis together with the aqueous phase. It was found that the presence of dense inorganic acid may even facilitate the separation in the liquid-liquid extraction equipment.

The mixture to be subjected to extraction in step i may further contain acetic acid less than 10% in weight, preferably less than 5% in weight, more preferably from 0 to 3% by weight, depending on the process used for the biomass degradation. Most of acetic acid will be transferred into the organic phase in liquid-liquid extraction, preferably less than 10% by weight of the originally present amount in the mixture remains in the aqueous phase.

The extracting agent according to the invention comprises at least one extracting solvent and/or at least one extracting reagent. The selection of the extraction reagent depends on separation efficiency due to different densities between the organic and aqueous phase, miscibility of the phases, dissolution of the solutes to the extracting agent depending on the polarity measured by dipole moment and dielectric constant. The boiling point of the extracting agent may be lower or higher than that of levulinic acid. The extracting agent may thus be pure extracting reagent, a mixture of extracting reagents, an effective extracting reagent in solvent or in solvent mixture, several extracting reagents in solvent or in solvent mixture. All commonly known extraction agents or their combinations and like agents used in liquid-liquid extraction satisfying the above mentioned criteria may be applied. As an example, suitable extraction agents may be found for example in Handbook of Solvent Extraction by Lo and Baird (1991), and especially for carboxylic acid extraction from aqueous solutions in U.S. Pat. No. 5,399,751, U.S. Pat. No. 4,401,514, US 2003/0036664, U.S. Pat. No. 4,217,460, WO02/053524, and especially for levulinic acid extraction in Shil'nikova and Sharkov, Angew. Chem. Chem. Fabrik (1965), 14, 147-51.

According to the invention, the aqueous acidic solution from biomass disintegration can be extracted with an extracting agent selected form the group of amines, amides, phosphine oxides, fatty acids or their esters, fatty alcohols, ketones, ethers, organophosphates and substituted urea derivatives. Preferred extracting agents are tertiary amines, secondary or tertiary amides, tertiary phosphine oxides, tertiary phosphates, $C_5$-$C_{12}$ fatty acids, $C_8$-$C_{12}$ fatty alcohols and alkyl urea derivatives. More preferred extracting agents are tertiary octyl-, hexyl- or octyl-hexyl-phosphine oxides such as Cyanex 923, or mixtures thereof, trioctyl phosphate, methyl ethyl ketone, octanol and tetrabutyl urea. In a preferred embodiment, extracting agents functioning as solvents are long chain aliphatic alkanes. More preferred extracting agents functioning as solvents are aliphatic hydrocarbons or aliphatic hydrocarbons with aromatic or aliphatic substituents or mixtures thereof, such as decane or kerosene or diphenylalkene.

It is preferred to carry out the extraction with a minimum amount of organic extracting agent since the higher the amounts of solutions in extraction and distillation the larger the equipment sizes and higher capital costs become. It is noted that the material requirements for the equipment are high due to the corrosive environment caused by formic and sulphuric acid. Materials, such as coated or cladded steels, zirconium, titanium and duplex are preferred. Furthermore, the lower the volume of solutions the lower the energy demand in distillation.

Any insoluble solids in the mixture to be extracted originating from the previous processes, for example tar, remain in the heavier aqueous phase.

In a preferred embodiment in the extraction step i, it is not required to remove all possible furfural, formic acid and levulinic acid because those chemicals may be recirculated in the aqueous phase back to previous process stages for biomass degradation, such as hydrolysis step. The aqueous phase to be recycled back comprises preferably up to 25% by weight furfural and up to 5% by weight levulinic acid compared to their infeed amount into the extraction step i, most preferably aqueous phase to be recycled back comprises essentially no furfural or levulinic acid. Since it is not necessary to obtain full recovery of chemicals in the liquid-liquid extraction, it is possible to reduce equipment and reagent costs and thus investment and operating costs.

In the liquid-liquid extraction step i, water, preferably 70%, more preferably 90%, most preferably 95% by weight, from the infeed aqueous liquid mixture is transferred into the aqueous phase.

As this aqueous phase is circulated back to biomass degradation such as hydrolysis, the organic phase (FIG. 1, flow 2) still containing some water is subjected to step ii (FIG. 1, B) if it contains furfural or to step iii (FIG. 1, C) if no furfural is present.

If the organic phase from step i contains furfural, this furfural is separated and recovered in step ii. Furfural to be recovered is separated by distillation wherein furfural and water are separated from the organic phase as furfural-water azeotrope vapour in the overhead of distillation column (FIGS. 1 and 2, B). The organic phase infeed (FIG. 1, flow 2) into furfural distillation step ii comprises water preferably not more than 5%, more preferably from 1 to 5%, most preferably from 1 to 4% by weight. The presence of this water is advantageous for the complete depletion of furfural from the organic phase. If there is not enough water in the infeed of this distillation step additional water infeed may be required.

The vaporized azeotropic furfural-water mixture is condensed and due to different densities two immiscible phases are formed in a decantation vessel or phase separation tank (FIG. 1, E). The aqueous phase is separated from the organic phase as lighter phase by gravitation. Furfural (FIG. 1, flow 10) is recovered from the organic phase in a form having a concentration of at least 80% by weight. At room temperature the furfural organic phase contains preferably at least 85% by weight of furfural, more preferably at least 90% by weight, most preferably 95% by weight, the balance being essentially water.

The aqueous phase from the decantation vessel contains preferably not more than 10% by weight furfural, the balance being essentially water. This aqueous phase (FIG. 1, flow 11) is preferably recycled and combined to the feed stream (FIG. 1, flow 2) prior to azeotropic distillation of furfural and thus adjusting the water-to-furfural ratio which is important for the formation of furfural-water azeotrope and efficient furfural separation.

Preferably, the furfural-water azeotropic distillation is performed in reduced pressure to increase the mass fraction of furfural. More preferably, this distillation is carried out under a reduced pressure of less than 500 mbar, most preferably between 100 to 300 mbar, since the mass fraction of furfural in the azeotrope is increased as pressure is decreased and the boiling point of the azeotrope is decreased.

It is most advantageous to perform the furfural azeotropic distillation prior to the formic acid removal and after the liquid-liquid extraction step as the furfural recovery requires the suitable amount of water for total removal of furfural from the organic phase and, on the other hand, formic acid recovery is facilitated by reducing the amount of water present to a minimum.

The residual bottom product, the furfural poor organic phase of furfural-water azeotropic distillation column (FIG. 1, B), is then directed to a further distillation column (FIG. 1, C) wherein formic acid is separated as such or partly as formic acid-water azeotrope from the mixture of extraction agent and levulinic acid.

In the step iii of the invention, formic acid is separated by distillation. The formic acid distillation may be performed in a conventional distillation column. The infeed preferably contains water to formic acid in a ratio of 1:1, preferably 1:6, or less. Concentrated formic acid is obtained as vapour (FIG. 1, flow 8) in the overhead of the distillation column and the vapour is condensed to obtain liquid formic acid. Formic acid is recovered as an essentially pure product and as a concentrated acid having a concentration of at least 50% by weight, preferably at least 85% by weight, more preferably at least 90% by weight, most preferably at least 95% by weight, from the organic infeed phase comprising further a mixture of levulinic acid and extracting agent which may be removed from the bottom of the distillation column. The obtained concentration of formic acid is essentially dependent on the amount of water in the organic infeed phase wherefrom formic acid is to be separated. In addition, the obtained concentration is dependent on chosen operating parameters such as temperature or pressure that is preferably below ambient pressure such as 1 bar, more preferably from 50 to 500 mbar, most preferably from 70 to 200 mbar, the energy input for the separation process and the reflux ratio which is preferably 10:1 or less, more preferably 5:1 or less, most preferably 1:1 or less.

The concentrated formic acid thus obtained may comprise trace amounts of impurities. Typically, some water remains in the acid, preferably less than 15%, more preferably less than 5% by weight. Depending on the operating parameters, some furfural may be remaining in the concentrated formic acid, preferably less than 200 ppm, more preferably less than 100 ppm. The raw material of the biomass process may include some volatile wood decomposition compounds that might produce minor amounts of impurities in the final formic acid product.

The separation of the furfural-water azeotrope may require some auxiliary agents to break the azeotrope.

The formic acid distillation column bottom product (FIG. 1, flow 4) comprising levulinic acid and the extracting agent and optionally acetic acid if it is present in the infeed mixture is passed to a further distillation column (FIG. 1, D).

In the step iv, levulinic acid is separated from the organic phase preferably by distillation. Levulinic acid is separated from the remaining extracting agent and any impurities still dissolved therein as overhead vapour (FIG. 2, flow 5) and the vapour is condensed to give liquid levulinic acid or liquid bottom product depending on the boiling point difference between levulinic acid and the selected extracting agent. If present, acetic acid will remain in the organic phase until levulinic acid is separated from the extracting reagent. Subsequently, acetic acid may be separated together with levulinic acid and further separated from levulinic acid by a further distillation step.

In the embodiment according to FIG. 1, levulinic acid with a lower boiling point compared to the extracting agent and thus being more volatile is obtained as the overhead product. The extracting agent remains in the bottom product and is recycled back to the liquid-liquid extraction of step i. If acetic acid is present in the feed mixture it will be co-distilled with levulinic acid as an overhead product. Subsequently, acetic acid may be separated together with levulinic acid and further separated from levulinic acid by a further distillation step. As it is preferred to recycle the extracting reagent as a pure product back to the liquid-liquid extraction step i this case is preferred.

In an embodiment according to FIG. 2, the extraction reagent having a lower boiling point and higher volatility than levulinic acid is distilled as an overhead product. This overhead product is recycled back to liquid-liquid extraction process. Levulinic acid is recovered as the bottom product. If acetic acid is present it may be separated with the extraction reagent and may be recycled back to extraction step i.

Alternatively, in the step iv, levulinic acid is separated from the organic phase preferably by neutralization with a base. This base comprises a basic metallic cation or ammonium ion, preferably said cation is from group I A or II A of the periodic table of elements, more preferably said cation is Na, K, Ca, Mg or ammonium which compounds have high solubility at high temperatures and show good performance in crystallisation and/or separation processes. Especially ammonium and potassium cations are especially preferred due to low cost and favourable residues such as gypsum, respectively. The base reacts with levulinic acid to produce the levulinate salt. Preferably, the process is a continuous process.

Figure 3:
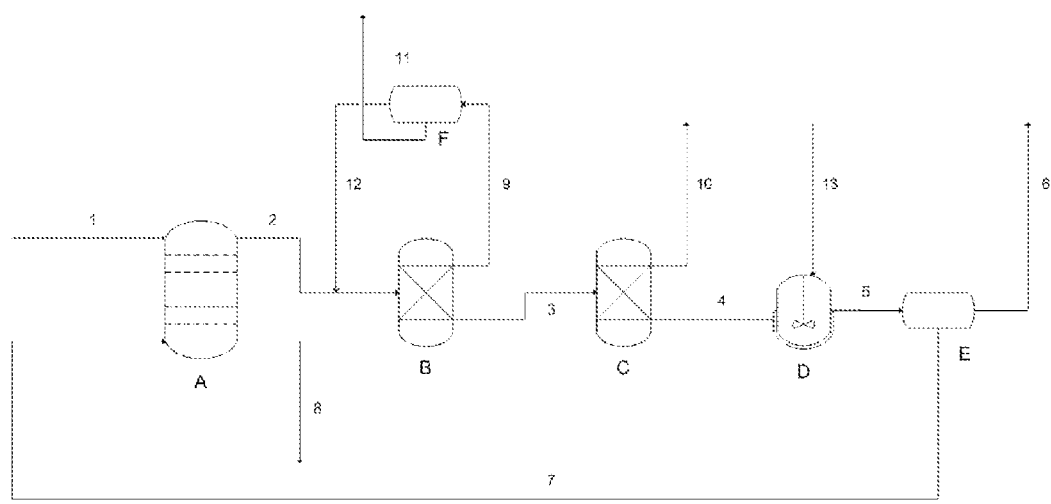
FIG. 3 is a schematic figure of a process for production of concentrated formic acid, furfural and levulinate salt, wherein extracting agent is separated by decantation from the levulinate salt solution.

Depending on the choice of the base, concentrations and/or reactants the formed levulinate either remains in solution as dissolved species or it precipitates into a solid. The neutralization reaction takes place in a reaction vessel, preferably in a mixing tank or in a pipe reactor equipped with static mixers (FIG. 3, D) or the like. An aqueous base solution is fed separately into the reaction vessel (FIG. 3, flow 13). If levulinate salt remains dissolved the resulting neutral mixture (FIG. 3, flow 5) from the reaction vessel is preferably led to decantation vessel or phase separation tank (FIG. 3, E) wherein phase separation occurs. Levulinate salt remains in the aqueous phase and is led out from the process and obtained as the product (FIG. 3, flow 6). The extracting agent (FIG. 3, flow 7) which contains up to 10% by weight, preferably up to 5%, more preferably from 1 to 5% water is led back to the extraction vessel (FIG. 3, A). Only a minor amount, preferably less than 1% by weight, of levulinate salt is present in this stream.

Figure 4:
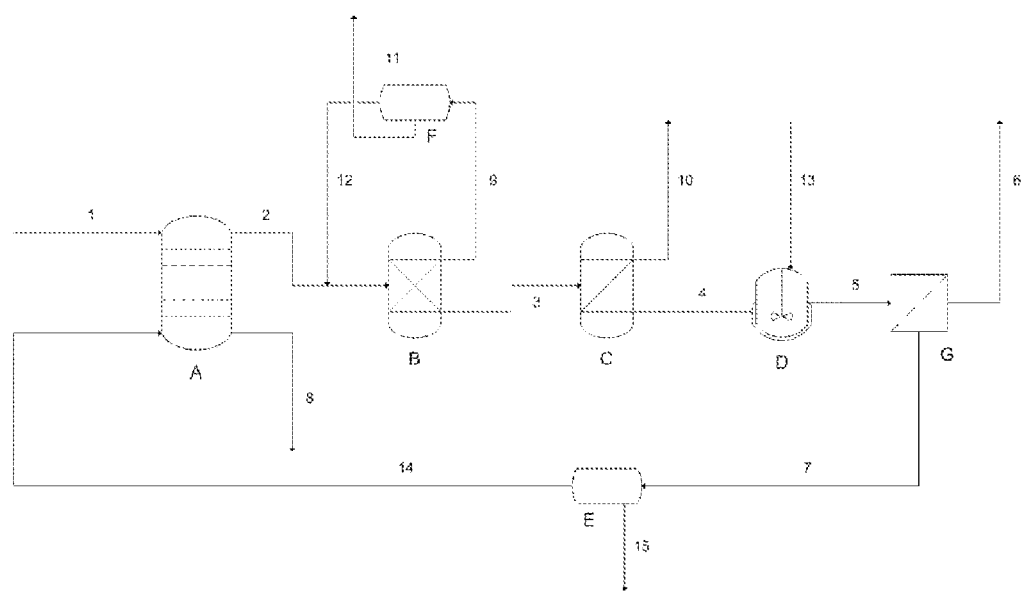
FIG. 4 is a schematic figure of a process for production of concentrated formic acid, furfural and levulinate salt, wherein an extracting agent is separated by filtration from the levulinate salt solution.

The neutral mixture (FIG. 4, flow 5) from the neutralization reactor (FIG. 4, D) is led in to the filtration equipment or in to the sentrifuge (FIG. 4, G) if the levulinate precipitates into solid phase. In the filtration equipment levulinate salt is separated and collected as the product (FIG. 4, flow 6). Filtrate (FIG. 4, flow 7) is led to the decantation vessel (FIG. 4, E) in which phase separation occurs. The extracting agent (FIG. 4, flow 14) which contains up to 10% by weight, preferably up to 5% more preferably from 1 to 5%, water is led back to extraction vessel (FIG. 4, A). Only minor amount of levulinate remains in this stream (FIG. 4, flow 14). Water rich aqueous phase (FIG. 4, flow 15) is led out for further use.

If the purities of the obtained products are not sufficient, auxiliary purification processes may be applied. These processes include conventional methods of distillation, stripping, adsorption, evaporation, crystallization and filtration. Especially for the purification of formic acid, adsorption to appropriate polymeric adsorption resins, such as aromatic polymer resin, for example, XAD4 and aliphatic polymer resins for example XAD7HP and XAD16 from the company Rohm & Haas Co. (now Dow Chemical, Inc), is efficient for the removal of traces of impurities, such as furfural.

There may be other methods or arrangements of implementation of the conceptual pre-treatment system than the one described here which are obvious modifications of the present invention for those skilled in the art and thus included in the present invention.

In a preferred embodiment of the invention, furfural-water azeotrope is separated from the organic phase comprising formic acid, furfural and levulinic acid by distillation in steps ii. The distillate is passed to the separation tank in which phase separation occurs. The light, upper phase comprises 10% by weight or less furfural, the balance being essentially water. This phase is recycled to the feed stream of furfural recovery distillation column B. From the heavy lower phase 95% or more of the extracted furfural having a purity over 90% by weight is recovered for further use. This process is depicted in FIG. 1. It is energy-efficient and thus a preferred processing method to recover furfural at a sufficiently low pressure, preferably 500 mbar or less. The yield of furfural recovery in distillation column B is high and it is preferred not to have residual furfural to be subjected to the following step iii together with formic acid. In every distillation column, the optimum column design and the selection of appropriate operation conditions: temperature, pressure, feed rate, reflux ratio, boiler efficiency and are of utmost importance.

In a yet further embodiment, liquid-liquid extraction step and distillation step are integrated to give an extractive distillation in the first distillation step, i.e. furfural distillation, wherein some of the previously mentioned extracting agents or mixtures thereof may be used in accordance to what is described in U.S. Pat. No. 4,692,219 disclosing the distillation of carboxylic acid mixture, namely acetic acid and formic acid mixture.

Alternatively, it is possible to combine reaction processes with the steps ii-iv wherein the separation of formic acid from the organic phase comprising furfural is facilitated by converting furfural by reaction into furfural derivatives, such as furfuryl alcohol, methyl furfuryl alcohol, methylfuran, furoic acid, furfurylamine, furan, and their further derivatives such as methyltetrahydrofuran or further into levulinic acid, preferably the reaction is carried out by catalytic hydrogenation. Hydrolysis with inorganic acids or oxidation reactions may be used parallel with or after hydrogenation in order to obtain the desired reaction product. In catalytic hydrogenation, catalyst effects may be provided by activated catalytic metals, preferably transition metals or mixtures thereof. The catalyst metal may be in pure metallic form or supported by appropriate support material. The reaction process may take place in a suspension or fixed bed type of gas-liquid reactor. Preferably, the fixed bed may be closely incorporated to the distillation column, so that the distillation and the reaction proceed simultaneously in the same equipment.

The concentrated formic acid obtained from step iii may be converted into derivatives of the acid, such as salts or esters. Furthermore, if a formic acid ester or salt, such as alkyl formate, ammonium formate or alkali metal formate, such as potassium formate, is the desired end product the salt or ester formation may be accomplished during the distillation step iii inside or outside the distillation column, preferably a sidestream is withdrawn from a selected separation stage of the distillation column and separately converted further into a salt, in a separate contacting device. The esterification or neutralization reaction may be accomplished by contacting the reactants, such as ethanol, ammonia gas or aqueous basic solution, such as alkali metal solution, with the organic acid solution on some of the upper separation stages of the distillation column or in a separate contacting device. Thus, pure formate ester or salt can be retrieved.

Different types of distillation column systems, such as various sequences of columns and modified column internals such as divided wall columns could be used to enhance the energy-efficiency of distillation.

The economy of the process means a low amount of water to be evaporated from the acid solution to render it concentrated.

EXAMPLES

The invention will be further illustrated by means of the following non-limiting examples.

Example 1

An aqueous liquid mixture of 99.12 g from acid hydrolysis of biomass comprising furfural, levulinic acid, formic acid and water was placed in a separating funnel at room temperature. Octanol, 67.14 g was added, and the mixture was vigorously shaken for 5 min. Separation into organic and aqueous phase took place after letting the filtrate stand for 5 minutes (min) and the two phases were removed into separate vessels. The mass of the aqueous phase was 92.26 g and that of the octanol phase was 73.63 g. An analysis of the concentrations is shown in Table 1.

TABLE 1

|  | Furfural, $g/kg_{solvent}$ | Levulinic acid, $g/kg_{solvent}$ | Formic acid, $g/kg_{solvent}$ | Water, $g/kg_{solvent}$ |
|---|---|---|---|---|
| Original mixture | 22.43 | 50.62 | 18.81 | 1000 |
| Aqueous phase | 8.14 | 0.0 | 0.0 | 1000 |
| Octanol phase | 21.64 | 68.26 | 25.40 | 58.12 |

Example 2

An aqueous liquid mixture of 112.57 g from acid hydrolysis of biomass comprising furfural, levulinic acid, formic acid and water was placed in a separating funnel at room temperature. TOF (tris-2-ethylhexylphosphate), 66.63 g was added, and the mixture was vigorously shaken for 5 min. Separation into organic and aqueous phase took place after letting the filtrate stand for 5 min and the two phases were removed into separate vessels. The mass of the aqueous phase was 106.98 g and that of the TOF phase was 71.23 g. An analysis of the concentrations is shown in Table 2.

TABLE 2

|  | Furfural, g/kg$_{solvent}$ | Levulinic acid, g/kg$_{solvent}$ | Formic acid, g/kg$_{solvent}$ | Water, g/kg$_{solvent}$ |
|---|---|---|---|---|
| Original mixture | 24.16 | 50.26 | 18.67 | 1000 |
| Aqueous phase | 7.27 | 0.0 | 0.0 | 1000 |
| TOF phase | 26.10 | 77.69 | 28.86 | 18.17 |

Example 3

A mixture of 1 kg consisting of 168.2 g/kg furfural, 504.3 g/kg levulinic acid, 170.1 g/kg formic acid and 157.4 g/kg water was placed in a batch distillation column. The mixture was boiled at a pressure of 500 mbar and the first fraction at the condenser temperature of 77° C. was collected from the stream from the condenser, and analyzed. This fraction consisted of two separable phases with essentially 100% by weight of furfural, calculated on the basis of organic components.

Distillation was continued and the second fraction at the condenser temperature of 84° C. was collected. The analysis of this fraction revealed that 94.5% by weight of it was formic acid and 5.5% by weight was furfural as calculated on the basis of organic components.

Example 4

A mixture of 1073 g consisting of 31.9 g/kg furfural, 79.4 g/kg levulinic acid, 29.4 g/kg formic acid, 74.6 g/kg water and 784.7 g/kg TOF was placed in a batch distillation column. The mixture was boiled at a pressure of 500 mbar and the first fraction at the condenser temperature of 77° C. was collected and analysed. This fraction consisted of two separable phases with essentially 100% by weight of furfural, calculated on the basis of organic components.

Distillation was continued and the mixture was boiled at a pressure of 85 mbar and the second fraction at the condenser temperature 55° C. was collected. The fraction was composed of 22% by weight of formic acid and 78% by weight of furfural, calculated on the basis of organic components.

Third fraction was collected at a pressure of 30 mbar and at the condenser temperature of 30° C. The analysis of organic compounds of this fraction revealed that 80% by weight of it was formic acid, 10.5% by weight was furfural and 9.5% by weight was levulinic acid.

Example 5

A mixture of 890 g consisting of 70.8 g/kg furfural, 16.85 g/kg levulinic acid, 64 g/kg formic acid, 247.2 g/kg water and 449.4 g/kg CYANEX 923 was placed in a bach distillation column. The mixture was boiled at a pressure of 500 mbar and the first fraction at the condenser temperature of 77° C. was collected and analysed. This fraction consisted of two separable phases with essentially 100% by weight of furfural, calculated on the basis of organic components.

Distillation was continued and the mixture was boiled at a pressure of 100 mbar and the second fraction at the condenser temperature 70° C. was collected. The analysis of this fraction revealed that 39% by weight of it was formic acid and 12% by weight was furfural, the balance being essentially water.

Third fraction was collected at a pressure of 70 mbar and at the condenser temperature of 30° C. The analysis of this fraction revealed that 86% by weight of it was formic acid and 1% by weight was furfural and 13% by weight was water.

In the bottom fraction, formic acid concentration remained as 6% by weight, furfural concentration remained as 2% by weight, water concentration remained as 1% by weight and levulinic acid remained as 91% by weight, calculated on the basis of all other components except CYANEX 923.

Example 6

A liquid mixture of 15.02 g levulinic acid and 85.02 g CYANEX 923 was shaken vigorously 5 min in the sepating funnel with 100.04 g base solution (a solution which originally consists of 44.13 g NaOH and 66.00 g water). Solid salt was formed. This salt was dissolved by adding 100.03 g water into the separation funnel. The final mixture was shaken 1 min. Separation into organic and aqueous phase took place after letting the filtrate stand for 5 min and the two phases were removed into separate vessels. The collected phases were weighted resulting in an organic phase of 92.18 g and a water phase of 206.48 g. Rest of the material remained in separation funnel. Levulinic acid analysis gave 6 weight percent (w-%) in the water phase and <0.5 w-% in the organic phase.

Example 7

A liquid mixture of 30.00 g levulinic acid and 70.01 g CYANEX 923 was shaken vigorously 5 min in the sepating funnel with 100.04 g base solution (a solution which originally consists of 44.11 g NaOH and 66.00 g water). Solid salt was formed. This salt was dissolved by adding 120.02 g water into the separation funnel. The final mixture was shaken 1 min. Separation into organic and aqueous phase took place after letting the filtrate stand for 5 min and the two phases were removed into separate vessels. The collected phases were weighted resulting in an organic phase of 72.53 g and a water phase of 246.35 g. Rest of the material remained in separation funnel. Levulinic acid content analysed was 11 w-% in the water phase and <0.5 w-% in the organic phase.

Example 8

A liquid mixture of 15.01 g levulinic acid and 85.02 g CYANEX 923 was shaken vigorously 5 min in the separating funnel with 100.04 g base solution (a solution which originally consists of 44.08 g KOH and 66.01 g water). Separation into the original organic and aqueous phase took place after letting the filtrate stand for 5 min and the two phases were removed into separate vessels. The original organic phase was then divided into two phases by centrifuging 20 min with 3000 rpm. The final organic phase was weighted (79.87 g) as well as the original water phase (46.29 g). Levulinic acid content analysed was 8 w-% in the original water phase and <0.5 w-% in the final organic phase.

Example 9

A liquid mixture of 30.02 g levulinic acid and 70.00 g CYANEX 923 was shaken vigorously 5 min in the separating funnel with 100.01 g base solution (a solution which originally consists of 44.09 g KOH and 66.00 g water). Separation into the original organic and aqueous phase took place after letting the filtrate stand for 5 min and the two phases were removed into separate vessels. The original organic phase was then divided into two phases by centrifuging 20 min with 3000 rpm. The final organic phase was weighted (64.26 g) as well as the original water phase (108.48 g). Levulinic acid content analysed was 17 w-% in the original water phase and <0.5 w-% in the final organic phase.

Example 10

An liquid mixture of 100.1 g from distillation experiments comprising CYANEX 923 (63-w-%), levulinic acid (29 w-%), formic acid (1.9 w-%) furfural (0.7 w-%), and water (0.35 w-%) was placed in a separating funnel at room temperature with 100.04 g base solution (a solution which originally consists of 40.04 g KOH and 160.00 g water) and 100.05 g water. The mixture was shaken vigorously 5 min. Separation into the organic and aqueous phase took place after letting it stand for 5 min and the first aqueous phase (220.46 g) was removed into separate vessel. The organic phase remained in separation funnel and 150.23 g water was added and mixture was shaken vigorously 5 min. Separation into the organic (83.54 g) and second aqueous phase (145.10 g) took place after letting it stand for 5 min. Two phases were removed into separate vessels and were weighted. Analysis of the phases is given in Table 3.

TABLE 3

|  | Levulinic acid, w-% | Formic acid, w-% | Furfural, w-% | Cyanex 923, mg/l |
|---|---|---|---|---|
| Aqueous phase 1 | 8.8 | 0.2 | <0.1 | 40 |
| Aqueous phase 2 | <0.1 | <0.1 | <0.1 | 110 |
| Organic phase | <0.1 | <0.1 | 2.0 |  |

The invention claimed is:

1. A method for separating and recovering concentrated formic acid from an aqueous liquid mixture containing formic acid, levulinic acid and up to 10% by weight furfural, obtained by degradation process of biomass, comprising:
   subjecting said mixture to liquid-liquid extraction process with an extracting agent, resulting in an organic phase comprising said extracting agent, formic acid, levulinic acid, furfural, and up to 5% by weight water, and an aqueous phase comprising essentially water;
   separating said aqueous phase from said organic phase;
   recovering furfural from said organic phase;
   recycling the aqueous phase formed in the furfural recovery back to an infeed of the furfural recovery;
   recovering formic acid in a form having a concentration of at least 50% by weight from said organic phase by distillation; and
   recovering levulinic acid or levulinate salt from said organic phase.

2. The method according to claim 1, further comprising recycling said extracting agent to the liquid-liquid extraction process.

3. The method according to claim 1, further comprising recycling said aqueous phase separated from the liquid-liquid extraction process back to the degradation process.

4. The method according to claim 1, wherein said biomass comprises cellulosic biomass material containing carbohydrates with components at least partly converted to furfural during the hydrolysis of said biomass.

5. The method according to claim 1, wherein said aqueous liquid mixture comprises formic acid up to 10% by weight, levulinic acid up to 15% by weight and furfural up to 10% by weight.

6. The method according to claim 1, wherein the furfural and/or levulinic acid is recovered by distillation and/or levulinate salt is recovered by neutralisation.

7. The method according to claim 1, wherein the extracting agent is selected separately or in any combination from the group consisting of tertiary amines, secondary or tertiary amides, tertiary phosphine oxides, tertiary phosphates, $C_5$-$C_{12}$ fatty acids, $C_8$-$C_{12}$ fatty alcohols, alkyl urea derivatives, long chain aliphatic hydrocarbons and aliphatic hydrocarbons with aromatic or aliphatic substituents.

8. The method according to claim 1, wherein said aqueous liquid mixture to said extracting agent is at a ratio from 1:1 to 4:1.

9. The method according to wherein said aqueous liquid mixture contains at least one inorganic acid.

10. The method according to claim 9, wherein the inorganic acid is in an amount up to 10% by weight.

11. The method according to claim 1, wherein the formic acid recovered is at a concentration of at least 85% by weight.

12. The method according to claim 1, wherein the levulinic acid is recovered in a form having a concentration of at least 50% by weight.

13. The method according to claim 1, wherein the furfural is recovered in a form having a concentration of at least 85% by weight.

14. The method according to claim 1, wherein the water and the formic acid are at a ratio of 1:6 or less in an infeed of the recovering of the formic acid.

* * * * *

UNITED STATES PATENT AND TRADEMARK OFFICE
CERTIFICATE OF CORRECTION

PATENT NO.        : 8,530,695 B2
APPLICATION NO. : 12/989001
DATED             : September 10, 2013
INVENTOR(S)       : Reunanen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this

Fifteenth Day of September, 2015

Michelle K. Lee
*Director of the United States Patent and Trademark Office*